United States Patent
Chiorini et al.

(10) Patent No.: US 11,447,797 B2
(45) Date of Patent: Sep. 20, 2022

(54) AAV WITH UNIQUE CAPSID PROTEIN VP1 AND METHODS OF USING FOR TREATMENT

(71) Applicant: The United States of America, as represented by the Secretary,Department of Health and Human Services, Bethesda, MD (US)

(72) Inventors: John A. Chiorini, Dayton, MD (US); Giovanni Di Pasquale, Kensington, MD (US); Randy Chandler, Chevy Chase, MD (US); Charles P. Venditti, Potomac, MD (US)

(73) Assignee: The United States of America,as represented by the Secretary, Department of Health and Human Service, Bethesda, MD (US)

( * ) Notice: Subject to any disclaimer, the term of this patent is extended or adjusted under 35 U.S.C. 154(b) by 654 days.

(21) Appl. No.: 15/573,214

(22) PCT Filed: May 12, 2016

(86) PCT No.: PCT/US2016/032047
§ 371 (c)(1),
(2) Date: Nov. 10, 2017

(87) PCT Pub. No.: WO2016/183297
PCT Pub. Date: Nov. 17, 2016

(65) Prior Publication Data
US 2018/0355376 A1    Dec. 13, 2018

Related U.S. Application Data

(60) Provisional application No. 62/331,699, filed on May 4, 2016, provisional application No. 62/160,552, filed on May 12, 2015.

(51) Int. Cl.
| | | |
|---|---|---|
| *A01N 63/00* | (2020.01) |
| *C12N 15/86* | (2006.01) |
| *C07K 14/635* | (2006.01) |
| *C12N 9/90* | (2006.01) |
| *A61P 5/14* | (2006.01) |
| *C07K 14/48* | (2006.01) |

(52) U.S. Cl.
CPC ............. *C12N 15/86* (2013.01); *A61P 5/14* (2018.01); *C07K 14/48* (2013.01); *C07K 14/635* (2013.01); *C12N 9/90* (2013.01); *C12Y 504/99002* (2013.01); *C07K 2319/02* (2013.01); *C12N 2750/14121* (2013.01); *C12N 2750/14122* (2013.01); *C12N 2750/14143* (2013.01)

(58) Field of Classification Search
USPC ......................................................... 424/93.1
See application file for complete search history.

(56) References Cited

U.S. PATENT DOCUMENTS

| | | |
|---|---|---|
| 4,797,368 A | 1/1989 | Carter et al. |
| 4,863,457 A | 9/1989 | Lee |
| 5,378,475 A | 1/1995 | Smith et al. |
| 5,443,505 A | 8/1995 | Wong et al. |
| 5,464,758 A | 11/1995 | Gossen et al. |
| 5,814,618 A | 9/1998 | Bujard et al. |
| 6,342,390 B1 | 1/2002 | Wiener et al. |
| 6,821,511 B2 | 11/2004 | Kotin et al. |
| 7,112,715 B2 | 9/2006 | Chambon et al. |
| 2003/0053990 A1 | 3/2003 | Rabinowitz et al. |
| 2008/0269149 A1 | 10/2008 | Bowles et al. |
| 2009/0202490 A1 | 8/2009 | Schaffer et al. |
| 2011/0104119 A1 | 5/2011 | Bowles et al. |

(Continued)

FOREIGN PATENT DOCUMENTS

| | | |
|---|---|---|
| JP | 2007507223 A | 3/2007 |
| JP | 2009535030 A | 10/2009 |

(Continued)

OTHER PUBLICATIONS

Bell (J. Virol., 2012, vol. 86, No. 13, p. 7326-7333).*
Senac (Gene Therapy, 2012, vol. 19, p. 385-391).*
Gabriel (Human Gene Therapy Methods, Apr. 2013, vol. 24, p. 80-93).*
Sen (J. Biomed. Sci. 2014, vol. 21, No. 103, p. 1-9).*
Xu (Histochem. Cell Biol. 2009, vol. 132, p. 239-246).*
Aslanidi (PLoS, Mar. 2013, vol. 8, No. 3, e59142).*
Adriaansen J. et al., "Human Parathyroid Hormone is Secreted Primarily into the Bloodstream After Rat Parotid Gland Gene Transfer," Human Gene Therapy, 22: 84-92 (2011).

(Continued)

*Primary Examiner* — Michael C Wilson
(74) *Attorney, Agent, or Firm* — Leydig Voit and Mayer, Ltd.

(57) ABSTRACT

The invention provides an adeno-associated viral (AAV) vector comprising a capsid comprising the amino acid sequence of SEQ ID NO: 4 or SEQ ID NO: 9, wherein the AAV vector further comprises a heterologous nucleic acid sequence, and wherein the heterologous nucleic acid sequence can encode the NGF-PTH fusion polypeptide or methylmalonyl CoA mutase enzyme. The invention also provides a polypeptide comprising nerve growth factor (NGF) signal peptide and parathyroid hormone (PTH), wherein the polypeptide can comprise, consist essentially of, or consist of the amino acid sequences of SEQ ID NO: 1 and SEQ ID NO: 2. The invention provides a nucleic acid encoding the polypeptide, a vector comprising the nucleic acid, and a composition comprising the polypeptide, nucleic acid, or vector, as well as treatment methods comprising the polypeptide, nucleic acid, vector, or composition. The invention further provides a method of treating methylmalonic acidaemia (MMA) in a mammal comprising administering an AAV vector comprising a heterologous nucleic acid sequence encoding methylmalonyl CoA mutase enzyme to the mammal.

12 Claims, 3 Drawing Sheets

Specification includes a Sequence Listing.

(56) References Cited

U.S. PATENT DOCUMENTS

| | | |
|---|---|---|
| 2014/0024671 A1 | 1/2014 | Eissenstat et al. |
| 2014/0199272 A1 | 7/2014 | Chiorini et al. |

FOREIGN PATENT DOCUMENTS

| | | | |
|---|---|---|---|
| WO | WO 2005/033321 | * | 4/2005 |
| WO | WO 2005/033321 A1 | | 4/2005 |
| WO | WO 2007/127264 A2 | | 11/2007 |
| WO | WO 2014/143884 A2 | | 9/2014 |
| WO | WO 2015/048534 A1 | | 4/2015 |
| WO | WO 2016/183297 A1 | | 11/2016 |

OTHER PUBLICATIONS

Beutler A. et al., "Retrovirus-Mediated Expression of an Artificial β-Endorphin Precursor in Primary Fibroblasts," *J. Neurochemistry*, 64: 475-481 (1995).

Daly T. et al., "Neonatal gene transfer leads to widespread correction of pathology i in a murine model of lysosomal storage disease", *Proc. Natl. Acad. Sci. U.S.A.*, 96: 2296-2300(1999).

Di Pasquale G. et al., "Sustained Exendin-4 Secretion through Gene Therapy Targeting Salivary Glands in Two Different Rodent Models of Obesity/Type 2 Diabetes," *PLoS ONE*, 7(7): e40074. doi:10.1371/journal.pone.0040074 (2012).

Di Pasquale G. et al., "Transduction of Salivary Gland Acinar Cells in Rodents with Adeno Associated Viral Vectors results in persistent Exocrine and Endocrine release of recombiant proteins," 2015 American Society of Gene & Cell Therapy (ASGCT) meeting abstract, published Apr. 27, 2015.

Forsberg et al., "Thrombin and H64A subtilisin cleavage of fusion proteins for preparation of human recombinant parathyroid hormone," *J. Protein Chem.*, 10(5): 517-26 (1991).

Fuhrmann-Benzakein E. et al., "Inducible and irreversible control of gene expression using a single transgene", *Nucleic Acids Res.*, 28(23):E99 (2000).

Fusion Protein 1 nr, Formatting Results—CYHZBA1701R. "Basic Local Alignment Search Tool", *BLAST®*, Feb. 25, 2016.

Fusion Protein 1 pat, Formatting Results—CYJFV21H01R, "Basic Local Alignment Search Tool", *BLAST®*, Feb. 25, 2016.

Gabriel N. et al., "Bioengineering of AAV2 Capsid at Specific Serine, Threonine, or Lysine Residues Improves Its Transduction Efficiency in Vitro and in Vivo", *Human Gene Therapy Methods*, 24:80-93 (2013).

Gao G. et al., "Clades of Adeno-Associated Viruses Are Widely Disseminated in Human Tissues, " *J. Virol.*, 78(12): 6381-6388 (2004).

GenBank Accession No. NP_000246 "Methylmalonyl-CoA mutase, mitochondrial precursor [*Homo sapiens*]" (2017).

Høgset A. et al., J Biol. Chem., Expression and Characterization of a Recombinant Human Parathyroid Hormone Secreted by *Escherichia coli* Employing the Staphylococcal Protein A Promoter and Signal Sequence. *J. Biol. Chem.*, 265(13): 7338-7344 (1990).

Im D. et al., "The AAV origin binding protein Rep68 is an ATP-dependent site-specific endonuclease with DNA helicase activity", *Cell*, 61: 447-57 (1990).

Indra A. et al., "Temporally-controlled site-specific mutagenesis in the basal layer of the epidermis: comparison of the recombinase activity of the tamoxifen-inducible Cre-$ER^T$ and Cre-$ER^{T2}$ recombinases", *Nucleic Acids Res.*, 27: 4324-4327 (1999).

International Search Report of International Application No. PCT/US2016/032047, dated Oct. 7, 2016.

Katano H. et al., "Identification of adeno-associated virus contamination in cell and virus stocks by PCR", *BioTechnigues*, 36:676-680 (2004).

Kramer B. et al., "Transgene Control Engineering in Mammalian Cells", *Methods Mol. Biol.*, 308: 123-144 (2005).

Li L. et al., "Production and Characterization of Novel Recombinant Adeno-Associated Virus Replicative-Form Genomes: A Eukaryotic Source of DNA for Gene Transfer", *PLOS One.*, 8(8): e69879. doi: 10.1371/journal.pone.0069879 (2013).

Niwa H. et al., "Efficient selection for high-expression transfectants with a novel eukaryotic vector", *Gene*, 108: 193-199 (1991).

No D. et al., "Ecdysone-inducible gene expression in mammalian cells and transgenic mice", *Proc. Natl. Acad. Sci.*, 93: 3346-3351 (1996).

Pereira D. et al., "The Adeno-Associated Virus (AAV) Rep Protein Acts as both a Repressor and an Activator To Regulate AAV Transcription during a Productive Infection", *J. Virol.*, 71: 1079-1088 (1997).

Protein Sequence (102 letters), Formatting Results—CYJJ2YSF01R, "Basic Local Alignment Search Tool", *BLAST®*, Feb. 25, 2016.

Protein Sequence (102 letters), Formatting Results—CYJNKXYP01R "Basic Local Alignment Search Tool", *BLAST®*, Feb. 25, 2016.

Salva M. et al., "Treating Hypoparathyroidism through Regulated Expression of Parathyroid Hormone in Skeletal Muscle", *Molecular Therapy, Nature Publishing Group*, GB, vol. 13 (2006), p. S83, XP005675322, ISSN: 1525-0016.

Sen D. et al., "Improving clinical efficacy of adeno associated vectors by rational capsid bioengineering", *Journal of Biomedical Science*, vol. 21, No. 103 (2014).

Schmidt M. et al., "Adeno-Associated Virus Type 12 (AAV12): a Novel AAV Serotype with Sialic Acid- and Heparan Sulfate Proteoglycan-Independent Transduction Activity▼", *Journal of Virology*, p. 1399-1406 (2008).

Schmidt M. et al., "Identification and characterization of novel adeno-associated virus isolates in ATCC virus stocks", *Journal of Virology*, 80(10):5082-5 (2006).

Sondhi D. et al., "Enhanced Survival of the LINCL Mouse Following CLN2 Gene : Transfer Using the rh.10 Rhesus Macaque-derived Adeno-associated Virus Vector", *Mol. Ther.*, 15: 481-491 (2007).

Wright J. et al., "Recombinant adeno-associated virus: formulation challenges and strategies for a gene therapy vector", *Curr. Opin. Drug Discov. Devel.*, 6(2): 174-178 (2003).

Wright J. et al., "Identification of Factors that Contribute to Recombinant AAV2 Particle Aggregation and Methods to Prevent Its Occurrence during Vector Purification and Formulation", *Molecular Therapy*, 12: 171-178 (2005).

Written Opinion of the International Searching Authority of International Application No. PCT/US2016/032047, dated Oct. 7, 2016.

Xu X. et al., "Human signal peptide had advantage over mouse in secretory expression," *Histochem. Cell Biol.*, 132(2): 239-246 (2009).Y Yamano S. et al., "Recombinant Adena-Associated Virus Serotype 2 Vectors Mediate Stable Interleukin 10 Secretion from Salivary Glands into the Bloodstream", *Human Gene Therapy*, vol. 13, No. 2, (2002), pp. 287-298, XP055290837, US ISSN: 1043-0342, DOI: 10.1089/10430340252769806.

Yang B. et al., "Global CNS transduction of adult mice by intravenously delivered rAAVrh.8 and rAAVrh.10 and nonhuman primates by rAAVrh.10", accepted manuscript, published online Apr. 30, 2014, for later publication in *Mol Ther.*, i 22(7): 1299-309 (2014) doi: 10.1038/mt.2014.68.

Zhong L. et al., "Next generation of adeno-associated virus 2 vectors: Point mutations in tyrosines lead to high-efficiency transduction at lower doses", *PNAS*, vol. 105, No. 22, pp. 7827-7832 (2008).

Japanese Patent Office, Office Action issued in Japanese Patent Application No. 2017-558710, 9 pages (dated Mar. 3, 2020).

* cited by examiner

AAV WITH UNIQUE CAPSID PROTEIN VP1 AND METHODS OF USING FOR TREATMENT

CROSS-REFERENCE TO RELATED APPLICATIONS

This patent application is a U.S. National Stage of PCT/US2016/032047, filed May 12, 2016, which claims the benefit of U.S. Provisional Patent Application No. 62/160,552, filed May 12, 2015, and U.S. Provisional Patent Application No. 62/331,699, filed May 4, 2016, each of which is incorporated by reference.

STATEMENT REGARDING FEDERALLY SPONSORED RESEARCH OR DEVELOPMENT

This invention was made with Government support under project number ZIADE000695-14 by the National Institutes of Health, National Institute of Dental and Craniofacial Research. The Government has certain rights in the invention.

SEQUENCE LISTING

Incorporated by reference in its entirety herein is a computer-readable nucleotide/amino acid sequence listing submitted concurrently herewith and identified as follows: One 30,708 Byte ASCII (Text) file named "730792_ST25.txt," dated Oct. 31, 2017.

BACKGROUND OF THE INVENTION

AAV is a member of the Parvoviridae family and comprises a linear, single-stranded DNA genome of less than about 5,000 nucleotides. AAV requires co-infection with a helper virus (i.e., an adenovirus or a herpes virus), or expression of helper genes, for efficient replication. AAV vectors used for administration of therapeutic nucleic acids typically have approximately 96% of the parental genome deleted, such that only the terminal repeats (ITRs), which contain recognition signals for DNA replication and packaging, remain. This eliminates immunologic or toxic side effects due to expression of viral genes. In addition, delivering specific AAV proteins to producing cells enables integration of the AAV vector comprising AAV ITRs into a specific region of the cellular genome, if desired (see, e.g., U.S. Pat. Nos. 6,342,390 and 6,821,511). Host cells comprising an integrated AAV genome show no change in cell growth or morphology (see, for example, U.S. Pat. No. 4,797,368).

The AAV ITRs flank the unique coding nucleotide sequences for the non-structural replication (Rep) proteins and the structural capsid (Cap) proteins (also known as virion proteins (VPs)). The terminal 145 nucleotides are self-complementary and are organized so that an energetically stable intramolecular duplex forming a T-shaped hairpin may be formed. These hairpin structures function as an origin for viral DNA replication by serving as primers for the cellular DNA polymerase complex. The Rep genes encode the Rep proteins Rep78, Rep68, Rep52, and Rep40. Rep78 and Rep68 are transcribed from the p5 promoter, and Rep 52 and Rep40 are transcribed from the p19 promoter. The Rep78 and Rep68 proteins are multifunctional DNA binding proteins that perform helicase and nickase functions during productive replication to allow for the resolution of AAV termini (see, e.g., Im et al., Cell, 61: 447-57 (1990)). These proteins also regulate transcription from endogenous AAV promoters and promoters within helper viruses (see, e.g., Pereira et al., J. Virol., 71: 1079-1088 (1997)). The other Rep proteins modify the function of Rep78 and Rep68. The cap genes encode the capsid proteins VP1, VP2, and VP3. The cap genes are transcribed from the p40 promoter.

The ability of AAV vectors to infect dividing and non-dividing cells and to establish long-term transgene expression, as well as the lack of pathogenicity, have made AAV vectors attractive for use in gene therapy applications.

The lack of cross-competition in binding experiments suggests that each AAV serotype has a distinct mechanism of entry into cells. Comparison of the capsid open reading frames (ORFs) from different serotypes has identified blocks of conserved and divergent sequence with most of the latter residing on the exterior of the virion, which explains the altered tissue tropism among AAV serotypes.

There is a desire for new AAV isolates with different host ranges and improved immunological properties.

Hypoparathyroidism is a hormone deficiency syndrome that leads to low blood calcium levels and high blood phosphorus levels for which current replacement therapy is inadequate.

There is a desire for new treatment methods for hypoparathyroidism.

BRIEF SUMMARY OF THE INVENTION

The invention provides an adeno-associated viral (AAV) vector comprising a capsid comprising the amino acid sequence of SEQ ID NO: 4 or SEQ ID NO: 9, wherein the AAV vector further comprises a heterologous nucleic acid sequence. In one aspect, the heterologous nucleic acid sequence encodes a NGF-PTH fusion polypeptide or methylmalonyl CoA mutase enzyme.

The invention provides a polypeptide comprising nerve growth factor (NGF) signal peptide and parathyroid hormone (PTH), wherein the polypeptide can comprise, consist essentially of, or consist of the amino acid sequences of SEQ ID NO: 1 and SEQ ID NO: 2. The invention also provides a nucleic acid encoding the polypeptide, a vector comprising the nucleic acid, and a composition comprising the polypeptide, nucleic acid, or vector.

The invention provides a method of treating hypoparathyroidism in a mammal comprising administering the polypeptide, nucleic acid, a vector, or composition to the mammal, thereby treating hypoparathyroidism in the mammal.

The invention provides a method of treating methylmalonic acidaemia (MMA) in a mammal comprising administering an AAV vector comprising a heterologous nucleic acid sequence encoding methylmalonyl CoA mutase enzyme.

BRIEF DESCRIPTION OF THE SEVERAL VIEWS OF THE DRAWING(S)

DETAILED DESCRIPTION OF THE INVENTION

Figure 1:
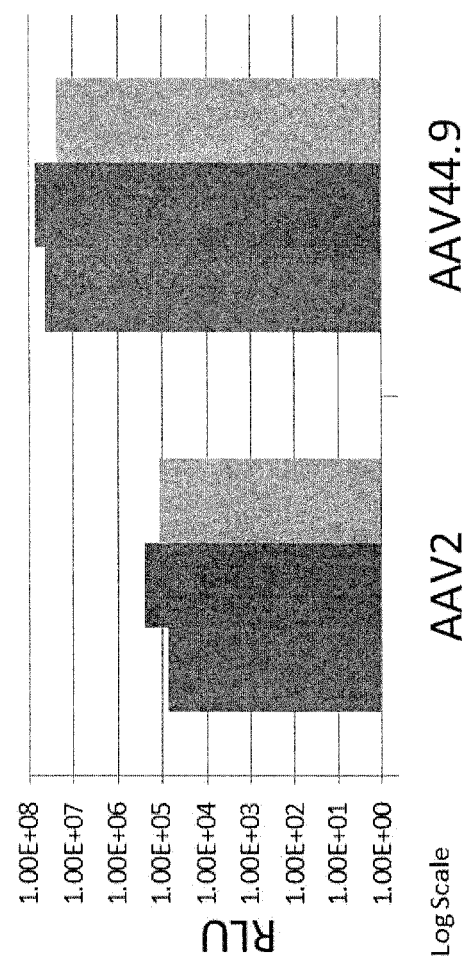
FIG. 1 is a graph demonstrating luciferase expression (RLU) of mice one month after administration of AAV CMV-luciferase particles (AAV2 or AAV 44.9) by cannulation in the right parotid salivary glands in 3 separate mice in each group.

The inventors have generated and characterized an AAV isolate termed "44-9." AAV 44.9 has high gene transfer activity in a number of cell types, including salivary gland cells, liver cells, and nerve cells (e.g., cells of the cortex, olfactory bulb, and brain stem and Purkinje cells of the cerebellum).

The amino acid sequence of capsid protein VP1 of AAV 44-9 differs from the amino acid sequence of capsid protein VP1 of the most closely reported isolate AAV rh8 (see Gao et al., J. Virol., 78(12): 6381-6388 (2004)) at several locations, two of which are serine residues in variable domain 3. In particular, the amino acid sequence of capsid protein VP1 of AAV 44-9 (SEQ ID NO: 4) differs at positions 179, 473, and 483 relative to the amino acid sequence of capsid protein VP1 of the most closely reported isolate AAV rh8 (SEQ ID NO: 6).

Mutagenesis studies of amino acids in the capsid proteins have suggested that some mutations have an inhibitory effect of the gene transfer activity of the vector, specifically the presence of serine and threonine residues in variable regions. Reports indicate that these amino acids increase the surface charge of the particles and target them for degradation in the lysosome, and that substitution with other non-charged amino acids can improve the transduction activity.

In view of the previous studies, it was unexpected that AAV 44-9 would have high gene transfer activity in a number of cell types given the inclusion of additional serine residues in variable domain 3 of capsid protein VP1 of AAV 44.9 (at positions 473 and 483 of SEQ ID NO: 4) relative to capsid protein VP1 of AAV rh8.

In one aspect, the invention provides a polypeptide comprising, consisting essentially of, or consisting of the amino acid sequence of SEQ ID NO: 4, which corresponds to capsid protein VP1 of AAV 44-9.

In another aspect, the invention provides a polypeptide comprising, consisting essentially of, or consisting of the amino acid sequence of SEQ ID NO: 9, which corresponds to capsid protein VP1 of AAV 44-9 with a substitution of the serine at position 470 with an asparagine. Although not wishing to be bound by any particular theory, the substitution is believed to alter the transduction and binding affinity of the AAV 44-9 comprising the mutated capsid protein. The desired substitution was achieved by using the QuikChange site-directed mutagenesis kit (Stratagene, San Diego, Calif.) and two complementary PCR primers. The forward primer has the nucleic acid sequence

AAGCAGGCCCTAGCAACATGGCCAGCC. (SEQ ID NO: 10)

Alterations of the amino acid sequence to produce variant polypeptides can be done by a variety of means known to those skilled in the art. For instance, amino acid substitutions can be conveniently introduced into the polypeptides at the time of synthesis. Alternatively, site-specific mutations can be introduced by ligating into an expression vector a synthesized oligonucleotide comprising the modified site. Alternately, oligonucleotide-directed, site-specific mutagenesis procedures can be used.

It is within the skill of the ordinary artisan to select synthetic and naturally-occurring amino acids that effect conservative or neutral substitutions for any particular naturally-occurring amino acids. The ordinarily skilled artisan desirably will consider the context in which any particular amino acid substitution is made, in addition to considering the hydrophobicity or polarity of the side-chain, the general size of the side chain and the pK value of side-chains with acidic or basic character under physiological conditions. For example, lysine, arginine, and histidine are often suitably substituted for each other, and more often arginine and histidine. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. This is because each of these amino acids are relatively hydrophobic when incorporated into a polypeptide, but glycine's lack of an α-carbon allows the phi and psi angles of rotation (around the α-carbon) so much conformational freedom that glycinyl residues can trigger changes in conformation or secondary structure that do not often occur when the other amino acids are substituted for each other. Other groups of amino acids frequently suitably substituted for each other include, but are not limited to, the group consisting of glutamic and aspartic acids; the group consisting of phenylalanine, tyrosine and tryptophan; and the group consisting of serine, threonine and, optionally, tyrosine. Additionally, the ordinarily skilled artisan can readily group synthetic amino acids with naturally-occurring amino acids.

The ordinarily skilled artisan can generate mutants or variants by, for example, substituting or mutating amino acids which are not critical for the anti-viral function of the polypeptide. Ideally, mutations that do not modify the electronic or structural environment of the peptide are generated to retain optimal activity. For example, amino acid residues which are not responsible for folding or stability of the three-dimensional conformation of the polypeptide are candidate residues for mutation.

If desired, the polypeptide of the invention can be modified, for instance, by glycosylation, amidation, carboxylation, or phosphorylation, or by the creation of acid addition salts, amides, esters, in particular C-terminal esters, and N-acyl derivatives of the proteins of the invention. The polypeptide also can be modified to create protein derivatives by forming covalent or noncovalent complexes with other moieties in accordance with methods known in the art. Covalently-bound complexes can be prepared by linking the chemical moieties to functional groups on the side chains of amino acids comprising the proteins, or at the N- or C-terminus. Desirably, such modifications and conjugations do not adversely affect the activity of the polypeptide.

The polypeptide can be prepared by any of a number of conventional techniques. The polypeptide can be isolated or purified from a recombinant source. For instance, a DNA fragment encoding a desired polypeptide can be subcloned into an appropriate vector using well-known molecular genetic techniques. The fragment can be transcribed and the polypeptide subsequently translated in vitro. Commercially available kits also can be employed. The polymerase chain reaction optionally can be employed in the manipulation of nucleic acids.

The polypeptide also can be synthesized using an automated peptide synthesizer in accordance with methods known in the art. Alternately, the polypeptide can be synthesized using standard peptide synthesizing techniques well-known to those of skill in the art. In particular, the polypeptide can be synthesized using the procedure of solid-phase synthesis. If desired, this can be done using an automated peptide synthesizer. Removal of the t-butyloxycarbonyl (t-BOC) or 9-fluorenylmethyloxycarbonyl (Fmoc) amino acid blocking groups and separation of the polypeptide from the resin can be accomplished by, for example, acid treatment at reduced temperature. The protein-containing mixture then can be extracted, for instance, with diethyl ether, to remove non-peptidic organic compounds, and the synthesized polypeptide can be extracted from the resin powder (e.g., with about 25% w/v acetic acid). Following the synthesis of the polypeptide, further purification (e.g., using HPLC) optionally can be performed in order to eliminate any incomplete proteins, polypeptides, peptides or free amino acids. Amino acid and/or HPLC analysis can be performed on the synthesized polypeptide to validate its identity. For other applications according to the invention, it may be preferable to produce the polypeptide as part of a larger fusion protein, either by chemical conjugation or through genetic means, such as are known to those skilled in the art. In this regard, the invention also provides a fusion protein comprising the polypeptide and one or more other protein(s) having any desired properties or functions, such as to facilitate isolation, purification, analysis, or stability of the fusion protein.

The invention also provides a nucleic acid encoding the inventive polypeptide or a variant thereof. In one embodiment, the nucleic acid comprises, consists essentially of, or consists of the nucleic acid sequence of SEQ ID NO: 5 (which sequence comprises multiple DNA fragments isolated from AAV 44-9). The nucleic acid (e.g., DNA, RNA, cDNA, and the like) can be produced in any suitable matter including, but not limited to recombinant production and commercial synthesis. In this respect, the nucleic acid sequence can be synthetic, recombinant, isolated, and/or purified.

The invention provides a vector comprising the nucleic acid. The nucleic acid can be inserted into any suitable vector. The selection of vectors and methods to construct them are commonly known in the art and are described in general technical references.

Suitable vectors include those designed for propagation and expansion or for expression or both. Examples of suitable vectors include, for instance, plasmids, plasmid-liposome complexes, CELid vectors (see, e.g., Li et al., *PLoS One.*, 8(8): e69879. doi: 10.1371/journal.pone. 0069879 (2013)) and viral vectors, e.g., parvoviral-based vectors (i.e., AAV vectors), retroviral vectors, herpes simplex virus (HSV)-based vectors, adenovirus-based vectors, and poxvirus vectors. Any of these expression constructs can be prepared using standard recombinant DNA techniques.

In one aspect of the invention, the vector is a viral vector, such as an AAV vector. In addition to the nucleic acid encoding the polypeptide, the vector can comprise one or more nucleic acid sequences encoding one or more polypeptides for delivery and expression in a host (e.g., a mammal, such as a mouse, rat, guinea pig, hamster, cat, dog, rabbit, pig, cow, horse, or primate (e.g., human)).

In a particular embodiment, the invention provides an AAV vector comprising a capsid comprising the polypeptide, wherein the AAV vector further comprises a heterologous nucleic acid sequence. In one embodiment, the AAV vector comprises a capsid comprising a VP1, VP2, and VP3 protein, wherein the VP1 protein comprises, consists essentially of, or consists of the amino acid sequence of SEQ ID NO: 4 or SEQ ID NO: 9, and wherein the AAV further comprises a heterologous nucleic acid sequence. The heterologous nucleic acid sequence can be flanked by one or more inverted terminal repeat (ITR) sequences. In one embodiment, the AAV vector comprises, consists essentially of, or consists of the nucleic acid sequence of SEQ ID NO: 5 (which sequence comprises multiple DNA fragments isolated from AAV 44-9).

A heterologous nucleic acid sequence refers to a nucleic acid sequence that is heterologous to the vector sequences flanking the heterologous nucleic acid sequence. The heterologous nucleic acid sequence can encode a polypeptide, protein, or other product of interest. The heterologous nucleic acid sequence is operatively linked to regulatory components in a manner which permits transcription, translation, and/or expression in a host cell.

The heterologous nucleic acid sequence can include a reporter sequence, which upon expression produces a detectable signal. Such reporter sequences include, without limitation, nucleic acid sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art to which high affinity antibodies directed thereto exist or can be produced by conventional means, and fusion proteins comprising a membrane bound protein appropriately fused to an antigen tag domain from, for example, hemagglutinin or Myc.

These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, when the sequence is the LacZ gene, the presence of the vector carrying the signal is detected by assays for beta-galactosidase activity. When the sequence encodes green fluorescent protein or luciferase, the vector carrying the signal may be measured visually by color or light production in a luminometer.

The heterologous nucleic acid sequence also can be a non-reporter sequence encoding a product which is useful in biology and medicine, such as proteins, peptides, RNA, enzymes, dominant negative mutants, or catalytic RNAs. Desirable RNA molecules include tRNA, dsRNA, ribosomal RNA, catalytic RNAs, siRNA, small hairpin RNA, trans-splicing RNA, and antisense RNAs. One example of a useful RNA sequence is a sequence which inhibits or extinguishes expression of a targeted nucleic acid sequence in the treated host. Typically, suitable target sequences include oncologic targets and viral diseases.

The heterologous nucleic acid sequence can be used to correct or ameliorate gene deficiencies, which may include deficiencies in which normal genes are expressed at less than normal levels or deficiencies in which the functional gene product is not expressed. For example, the heterologous nucleic acid sequence can encode a therapeutic protein or polypeptide which is expressed in a host cell (e.g., PTH, methylmalonyl CoA mutase enzyme (e.g., GeneBank Accession No. NP_000246), or retinoschisin).

Suitable heterologous nucleic acid sequences may be readily selected by one of skill in the art. The selection of the heterologous nucleic acid sequence is not considered to be a limitation of this invention. In particular, the heterologous nucleic acid sequence can be a nucleic acid sequence encoding an NGF-PTH fusion polypeptide as described herein, methylmalonyl CoA mutase enzyme, retinoschisin, aquaporin 1, aquaporin 5, coagulation factor IX, Xa, insulin, Ex4, human growth hormone, alpha 1 anti-trypsin, bmp6 antagonists, CRSPRi or CRISPRa guide RNAs, modified Cas that can regulate the expression of the listed endogenous genes, and/or antibodies. In one embodiment, the heterologous nucleic acid sequence comprises the nucleic acid sequence of SEQ ID NO: 3.

The heterologous nucleic acid sequence can encode one or more polypeptides, wherein the one or more polypeptides comprises a signal peptide/leader peptide such as the modified heavy chain leader sequence of SEQ ID NO: 11, the leader sequences of coagulation factor IX, PTH, human growth hormone (e.g., the leader sequence missing the first 6 amino acids), guassia, and insulin, the AppS4 synthetic yeast leader sequence of SEQ ID NO: 12, or a NGF signal peptide (e.g., the NGF signal peptide of SEQ ID NO: 1). In one embodiment, the heterologous nucleic acid sequence encodes a fusion polypeptide comprising PTH and a signal peptide/leader peptide such as the modified heavy chain leader sequence of SEQ ID NO: 11, the leader sequences of coagulation factor IX, PTH, human growth hormone (e.g., the leader sequence missing the first 6 amino acids), guassia, and insulin, or the AppS4 synthetic yeast leader sequence of SEQ ID NO: 12 (e.g., the NGF signal peptide of the NGF-PTH fusion polypeptide is substituted with a different signal peptide).

The heterologous nucleic acid sequence (e.g., encoding the NGF-PTH fusion polypeptide described herein) can be flanked by one or more inverted terminal repeat (ITR) sequences.

The vector (e.g., AAV vector) can comprise multiple (two, three, four, five, six, seven, eight, nine, or ten) heterologous nucleic acid sequences. Multiple heterologous nucleic acid sequences can be used, for example, to correct or ameliorate a gene defect caused by a multi-subunit protein. In certain situations, a different heterologous nucleic acid sequence may be used to encode each subunit of a protein, or to encode different peptides or proteins. This is desirable when the size of the nucleic acid encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same nucleic acid sequence. In this case, a single heterologous nucleic acid sequence includes the nucleic acid encoding each of the subunits, with the nucleic acid for each subunit separated by an internal ribozyme entry site (IRES). This is desirable when the size of the nucleic acid encoding each of the subunits is small, e.g., the total size of the nucleic acid encoding the subunits and the IRES is less than five kilobases. As an alternative to an IRES, the nucleic acid may be separated by sequences encoding a 2A peptide, which self-cleaves in a post-translational event. This 2A peptide is significantly smaller than an IRES, making it well suited for use when space is a limiting factor. More often, when the heterologous nucleic acid sequence is large, consists of multi-subunits, or two heterologous nucleic acid sequences are co-delivered, rAAV carrying the desired heterologous nucleic acid sequence(s) or subunits are co-administered to allow them to concatamerize in vivo to form a single vector genome. In such an embodiment, a first AAV vector may carry an expression cassette which expresses a single heterologous nucleic acid sequence and a second AAV vector may carry an expression cassette which expresses a different heterologous nucleic acid sequence for co-expression in the host cell. However, the selected heterologous nucleic acid sequence may encode any biologically active product or other product, e.g., a product desirable for study.

Desirably, the vector (e.g., AAV vector) comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

The vector (e.g., AAV vector) preferably comprises expression control sequences, such as promoters, enhancers, polyadenylation signals, transcription terminators, internal ribosome entry sites (IRES), and the like, that provide for the expression of the nucleic acid sequence(s) in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, and the RSV promoter. Inducible promoters include, for example, the Tet system (U.S. Pat. Nos. 5,464,758 and 5,814,618), the Ecdysone inducible system (No et al., *Proc. Natl. Acad. Sci.,* 93: 3346-3351 (1996)), the T-REX™ system (Invitrogen, Carlsbad, Calif.), LACSWITCH™ System (Stratagene, San Diego, Calif.), and the Cre-ERT tamoxifen inducible recombinase system (Indra et al., *Nuc. Acid. Res.,* 27: 4324-4327 (1999); *Nuc. Acid. Res.,* 28: e99 (2000); U.S. Pat. No. 7,112,715; and Kramer & Fussenegger, *Methods Mol. Biol.,* 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. For example, the nucleic acid encoding the polypeptide can be operably linked to a CMV enhancer/chicken β-actin promoter (also referred to as a "CAG promoter") (see, e.g., Niwa et al., Gene, 108: 193-199 (1991); Daly et al., Proc. Natl. Acad. Sci. U.S.A., 96: 2296-2300 (1999); and Sondhi et al., Mol. Ther., 15: 481-491 (2007)).

The inventors have generated and characterized a fusion polypeptide comprising the signal peptide of nerve growth factor (NGF) and parathyroid hormone (PTH). The NGF and PTH can be mammalian (e.g., mouse, rat, or human). In one embodiment, the fusion polypeptide comprises the amino acid sequence of SEQ ID NO: 1 (corresponding to the NGF signal peptide) and the amino acid sequence of SEQ ID NO: 2 (corresponding to PTH 1-84). Thus, in one aspect, the invention provides a polypeptide comprising, consisting essentially of, or consisting of the amino acid sequence of SEQ ID NO: 1 and the amino acid sequence of SEQ ID NO: 2.

The NGF-PTH fusion polypeptide additionally can comprise one or more linker sequences. Any suitable linker sequences can be used including but not limited to linkers comprising multiple glycine residues, multiple serine residues, or a combination thereof.

As described herein, alterations of the amino acid sequence to produce variant polypeptides can be done by a variety of means known to those skilled in the art.

The NGF-PTH polypeptide can be prepared by any of a number of conventional techniques as described herein.

The invention also provides a nucleic acid encoding the NGF-PTH polypeptide or a variant thereof. The nucleic acid (e.g., DNA, RNA, cDNA, and the like) can be produced in any suitable matter including, but not limited to recombinant production and commercial synthesis. In this respect, the nucleic acid sequence can be synthetic, recombinant, isolated, and/or purified. In one embodiment, nucleic acid encoding the polypeptide comprises the nucleic acid sequence of SEQ ID NOs: 7 and 8.

The invention provides a vector comprising the nucleic acid. The nucleic acid can be inserted into any suitable vector as described herein. In one aspect of the invention, the vector is a viral vector, such as an AAV vector. In one embodiment, the AAV vector is AAV8, AAV9, or rh10. In another embodiment, the vector is the AAV 44.9 vector described herein.

In addition to, or as an alternative to, the nucleic acid encoding the NGF-PTH fusion polypeptide, the vector can comprise one or more heterologous nucleic acid sequences encoding one or more polypeptides for delivery and expression in a host as described herein.

The invention provides a composition comprising, consisting essentially of, or consisting of one or more of the inventive polypeptides, nucleic acids, or vectors and a pharmaceutically acceptable (e.g. physiologically acceptable) carrier. When the composition consists essentially of one or more of the inventive polypeptides, nucleic acids, or vectors and a pharmaceutically acceptable carrier, additional components can be included that do not materially affect the composition (e.g., adjuvants, buffers, stabilizers, anti-inflammatory agents, solubilizers, preservatives, etc.). When the composition consists of one or more of the inventive polypeptides, nucleic acids, or vectors and the pharmaceutically acceptable carrier, the composition does not comprise any additional components.

Any suitable carrier can be used within the context of the invention, and such carriers are well known in the art. The choice of carrier will be determined, in part, by the particular site to which the composition may be administered and the particular method used to administer the composition. The composition optionally can be sterile with the exception of the vector described herein. The composition can be frozen or lyophilized for storage and reconstituted in a suitable sterile carrier prior to use. The compositions can be generated in accordance with conventional techniques described in, e.g., Remington: The Science and Practice of Pharmacy, 21st Edition, Lippincott Williams & Wilkins, Philadelphia, Pa. (2001).

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the carrier is a buffered saline solution. More preferably, the polypeptide, nucleic acid, or vector is administered in a composition formulated to protect the polypeptide, nucleic acid, or vector from damage prior to administration. For example, the composition can be formulated to reduce loss of the polypeptide, nucleic acid, or vector on devices used to prepare, store, or administer the polypeptide, nucleic acid, or vector, such as glassware, syringes, or needles. The composition can be formulated to decrease the light sensitivity and/or temperature sensitivity of the polypeptide, nucleic acid, or vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the polypeptide, nucleic acid, or vector, facilitate administration, and increase the efficiency of the inventive method. Formulations for polypeptide, nucleic acid, or vector-containing compositions are further described in, for example, Wright et al., Curr. Opin. Drug Discov. Devel., 6(2): 174-178 (2003) and Wright et al., Molecular Therapy, 12: 171-178 (2005)).

The composition also can be formulated to enhance transduction efficiency. In addition, one of ordinary skill in the art will appreciate that the one or more of the inventive polypeptides, nucleic acids, or vectors can be present in a composition with other therapeutic or biologically-active agents. For example, factors that control inflammation, such as ibuprofen or steroids, can be part of the composition to reduce swelling and inflammation associated with in vivo administration of one or more of the inventive polypeptides, nucleic acids, or vectors. Antibiotics, i.e., microbicides and fungicides, can be present to treat existing infection and/or reduce the risk of future infection, such as infection associated with gene transfer procedures.

Any route of administration can be used to deliver the composition to the host. Indeed, although more than one route can be used to administer the composition, a particular route can provide a more immediate and more effective reaction than another route. The composition can be administered by oral, aerosol, transdermal, parenteral (e.g., subcutaneous, intravenous, intraarterial, intramuscular, intradermal, interperitoneal, and intrathecal), rectal, and vaginal administration.

The composition can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the polypeptide, nucleic acid, or vector. The composition also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

The dose of the one or more of the inventive polypeptides, nucleic acids, or vectors in the composition administered to the host will depend on a number of factors, including the size (mass) of the host, the extent of any side-effects, the particular route of administration, and the like. Preferably, the inventive method comprises administering a "therapeutically effective amount" of the composition comprising the one or more of the inventive polypeptides, nucleic acids, or vectors described herein. A "therapeutically effective amount" refers to an amount effective, at dosages and for periods of time necessary, to achieve a desired therapeutic result. The therapeutically effective amount may vary according to factors such as the age, sex, and weight of the individual, and the ability of the polypeptide, nucleic acid, or vector to elicit a desired response in the individual. In another embodiment, the inventive method can comprise administering a "prophylactically effective amount" of the composition comprising the one or more of the inventive polypeptides, nucleic acids, or vectors. A "prophylactically effective amount" refers to an amount effective, at dosages and for periods of time necessary, to achieve a desired prophylactic result. The dose of vector in the composition required to achieve a particular therapeutic or prophylactic effect typically is administered in units of vector genome copies per cell (gc/cell) or vector genome copies/per kilogram of body weight (gc/kg). An ordinarily skilled artisan can readily determine an appropriate polypeptide, nucleic acid, or vector dose range to treat a patient having a particular disease or disorder based on these and other factors that are well known in the art.

In one embodiment, the composition is administered once to the host. In another embodiment, it may be appropriate to administer the composition multiple times during a therapeutic period and/or employ multiple administration routes, e.g., intramuscular and subcutaneous, to ensure sufficient exposure of cells to the composition. For example, the composition may be administered to the host two or more times (e.g., 2, 3, 4, 5, 6, 6, 8, 9, or 10 or more times) during a therapeutic period. The composition can be administered in conjunction with one or more additional agents.

In one embodiment, the NGF-PTH fusion polypeptide, nucleic acid, vector, or composition is administered to a host (e.g., mammal) to treat hypoparathyroidism.

In another embodiment, a vector (e.g., an AAV 44.9 vector as described herein) encoding methylmalonyl CoA mutase enzyme or composition comprising the vector is administered to a host (e.g., mammal) to treat (e.g., improve) impaired B12 metabolism. In particular, an AAV 44.9 vector encoding methylmalonyl CoA mutase enzyme can be administered (e.g., transdermally administered) to the liver, which results in a significant decrease in circulating methylmalonic acid levels and the treatment of methylmalonic acidaemia (MMA).

Additionally, a vector (e.g., AAV 44.9 vector) encoding retinoschisin can be administered to a host (e.g., mammal) to treat retinoschisis in the eye.

The following examples further illustrate the invention but, of course, should not be construed as in any way limiting its scope.

Example 1

This example describes the generation of the AAV 44.9 isolate.

The capsid ORF for AAV 44-9, which contained a functional promoter to drive expression, was PCR amplified a pool of viral DNA and then cloned into a plasmid vector. To be useful in making a recombinant vector, this plasmid was combined with two others that contain parts from other AAV isolates: a plasmid from AAV 12 (rep26), which encodes the proteins necessary for replication of the viral genome, and a plasmid, which has the origins of replication from AAV2 flanking a gene of interest (heterologous nucleic acid sequence).

It was uncertain whether this chimeric virus approach would work as some AAVs, such as AAV5, BAAV and AAAV, have unique ITRs and rep proteins and they might not work with the AAV 44-9 capsid protein as there are studies supporting an interaction between the rep and cap. Also there is an additional internal ORF within the capsid ORF that produces a protein called AAP and is reported to be required for efficient capsid assembly.

The ITRs which serve as the viral origin of replication and are required for packaging were removed from the viral genome and added to the gene of interest (heterologous nucleic acid sequence). Additionally, the ORF for replication proteins were separated from the capsid ORF to prevent recombination and improve vector yield.

Example 2

This example demonstrates the use of the AAV 44.9 isolate as a gene transfer vector into cells that are currently not efficiently targeted for gene transfer.

(a) In Vitro Versus In Vivo

Using the nucleic acid encoding the AAV 44.9 capsid, a recombinant vector carrying a CMV-Luc reporter gene cassette was generated. The virus production yield was equal or superior to other AAV types tested.

Biological activity (generation of luciferase activity) of the rAAV 44.9 CMV-Luc in tissue culture cells, such as 293T and COS, was poor; however, in vivo intraperitoneal administration ($5 \times 10^9$ viral particles) resulted in robust and rabid luciferase expression (RLU).

(b) AAV 44.9 Transduces Salivary Glands $2 \times 10^{10}$ AAV CMV-Luc particles (AAV2 or AAV 44.9) were administered by cannulation in the right parotid salivary glands of mice. One month later, Luc activity was measured by Xenogen imaging. As is clear from FIG. 1, AAV 44.9 demonstrated increased gene transfer ability when compared to AAV2.

In a similar experiment, $2 \times 10^{11}$ CMV CRE particles (AAV2 or AAV 44.9) were administered by cannulation in the right parotid salivary glands of tomato-floxed membrane-GFP transgenic mice. One month later, transduction was observed as green cells rather than tomato-labeled cells by confocal microscopy imaging. AAV 44.9 demonstrated increased gene transfer ability when compared to AAV2.

(c) AAV 44.9 Transduces Cells of CNS $4 \times 10^{10}$ scAAV CMV-GFP particles were injected in mice CNS. AAV 44.9 transduction was distributed all over the brain. Positive cells were observed in the cortex, olfactory bulb, and brain stem and in Purkinje cells of the cerebellum following intraventricular injection.

Example 3

This example demonstrates endocrine release of the NGF-PTH fusion polypeptide after single parotid salivary gland cannulation of an AAV vector containing the CMV NGF-PTH gene cassette of SEQ ID NO: 3.

Figure 2:
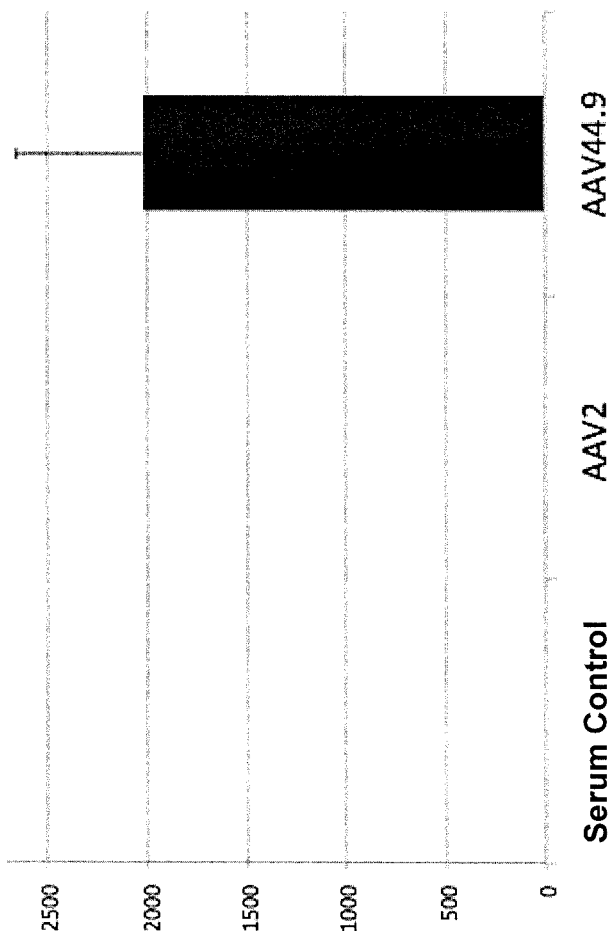
FIG. 2 is a graph demonstrating luciferase expression (pg/mL) in 293 cells stably transfected with the PTH receptor and a CREB Responsive Element (CRE) promoter driving a firefly luciferase reporter gene that were incubated for five hours with serum from AAV2, AAV 44.9, or control GFP cannulated mice.

Nine months after AAV administration, PTH secretion was quantified by a PTH biological assay. Briefly, 293 cells stably transfected with a PTH receptor and a CREB responsive element (CRE) promoter driving a firefly luciferase reporter gene were incubated for five hours with serum from AAV2, AAV 44.9, or control GFP cannulated mice. The luciferase expression was converted to pg/ml using a standard curve of PTH added in serum from untreated mice and the results shown in FIG. 2.

The AAV 44.9 vector was able to direct long term expression from the salivary gland. In particular, therapeutic levels of biologically active hormone were produced for over 8 months. Indeed, circulating levels of PTH at 3.56 ng/mL±1.032 were produced in mice, which is 1000 times the normal circulating levels. This differs from previous studies showing only transient expression (see, e.g., Adriaansen et al., *Human Gene Therapy*, 22: 84-92 (2011)).

Thus, the AAV 44.9 vector can be successfully delivered to salivary glands and the heterologous nucleic acid sequence expressed, e.g., for the treatment of hypoparathyroidism.

Example 4

This example demonstrates that AAV 44.9 vector can be used for delivery to the liver.

Figure 3:
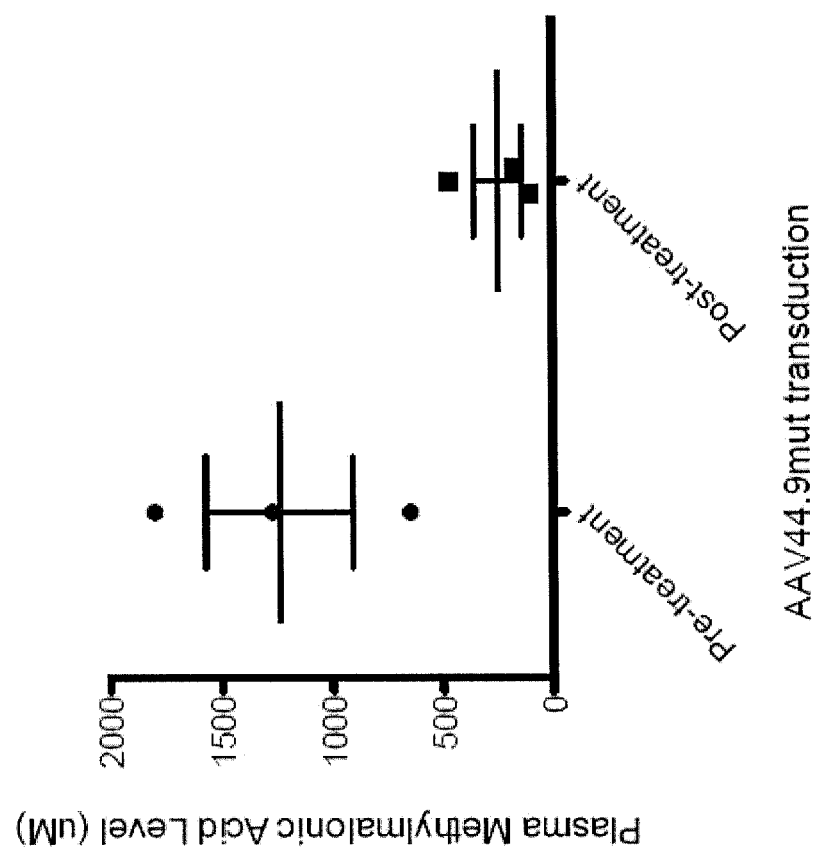
FIG. 3 is a graph demonstrating plasma methylmalonic acid level (μM) in neonatal mice with a deficiency in methylmalonyl CoA mutase enzyme before and after transdemial administration to the liver of an AAV 44.9 vector encoding methylmalonyl CoA mutase enzyme.

An AAV 44.9 vector encoding methylmalonyl CoA mutase enzyme was delivered transdermally to the liver of neonatal mice with a deficiency in methylmalonyl CoA mutase enzyme (resulting in impaired B12 metabolism). As demonstrated in FIG. 3, a significant decrease in circulating methylmalonic acid levels was observed following delivery.

Thus, the AAV 44.9 vector can be successfully delivered to the liver and the heterologous nucleic acid sequence expressed, e.g., for the treatment of the liver disorder methylmalonic acidaemia (MMA).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An adeno-associated viral (AAV) vector comprising a nucleic acid encoding a capsid comprising the amino acid sequence of SEQ ID NO: 4 or SEQ ID NO: 9, wherein the AAV vector further comprises a heterologous nucleic acid sequence.

2. The AAV vector of claim 1, wherein the heterologous nucleic acid sequence is operably linked to regulatory sequences which direct its expression in a host cell.

3. The AAV vector of claim 1, wherein the heterologous nucleic acid sequence is flanked by one or more inverted terminal repeat (ITR) sequences.

4. The AAV vector of claim 1, wherein the nucleic acid encoding the capsid comprises the nucleic acid sequence of SEQ ID NO: 5.

5. The AAV vector of claim 1, wherein the heterologous nucleic acid sequence encodes methylmalonyl CoA mutase enzyme.

6. A method of treating methylmalonic acidaemia (MMA) in a mammal with MMA comprising intravenously administering to the mammal the vector of claim 5, thereby treating MMA in the mammal.

7. The AAV vector of claim 1, wherein the heterologous nucleic acid sequence encodes a polypeptide comprising nerve growth factor (NGF) signal peptide and parathyroid hormone (PTH).

8. The AAV vector of claim 7, wherein the polypeptide comprises the amino acid sequences of SEQ ID NO: 1 and SEQ ID NO: 2.

9. A method of treating hypoparathyroidism in a mammal comprising administering the AAV vector of claim 7 to the salivary glands of the mammal, thereby treating hypoparathyroidism in the mammal.

10. A composition comprising the AAV vector of claim 1 and a pharmaceutically acceptable carrier.

11. The vector of claim 1, wherein the adeno-associated viral vector comprises a nucleic acid encoding a capsid protein (i) comprising the amino acid sequence of SEQ ID NO: 4 or (ii) encoded by the nucleic acid sequence of SEQ ID NO: 5.

12. The vector of claim 1, wherein the adeno-associated viral vector comprises a nucleic acid encoding a capsid protein comprising the amino acid sequence of SEQ ID NO: 9.

* * * * *

SEQUENCE LISTING

```
<160> NUMBER OF SEQ ID NOS: 12

<210> SEQ ID NO 1
<211> LENGTH: 121
<212> TYPE: PRT
<213> ORGANISM: Artificial Sequence
<220> FEATURE:
<223> OTHER INFORMATION: Synthetic

<400> SEQUENCE: 1

Met Ser Met Leu Phe Tyr Thr Leu Ile Thr Ala Phe Leu Ile Gly Val
1               5                   10                  15
```

```
Gln Ala Glu Pro Tyr Thr Asp Ser Asn Val Pro Glu Gly Asp Ser Val
            20                  25                  30

Pro Glu Ala His Trp Thr Lys Leu Gln His Ser Leu Asp Thr Ala Leu
        35                  40                  45

Arg Arg Ala Arg Ser Ala Pro Thr Ala Pro Ile Ala Ala Arg Val Thr
50                  55                  60

Gly Gln Thr Arg Asn Ile Thr Val Asp Pro Arg Leu Phe Lys Lys Arg
65                  70                  75                  80

Arg Leu His Ser Pro Arg Val Leu Phe Ser Thr Gln Pro Pro Thr
                85                  90                  95

Ser Ser Asp Thr Leu Asp Leu Asp Phe Gln Ala His Gly Thr Ile Pro
            100                 105                 110

Phe Asn Arg Thr His Arg Ser Lys Arg
            115                 120

<210> SEQ ID NO 2
<211> LENGTH: 84
<212> TYPE: PRT
<213> ORGANISM: Artificial Sequence
<220> FEATURE:
<223> OTHER INFORMATION: Synthetic

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 3
<211> LENGTH: 1259
<212> TYPE: DNA
<213> ORGANISM: Artificial Sequence
<220> FEATURE:
<223> OTHER INFORMATION: Synthetic

<400> SEQUENCE: 3
```

| | | | | | |
|---|---|---|---|---|---|
| ctcaatgggc | gtggatagcg | gtttgactca | cggggatttc | caagtctcca | ccccattgac | 60 |
| gtcaatggga | gtttgttttg | gcaccaaaat | caacgggact | ttccaaaatg | tcgtaacaac | 120 |
| tccgccccat | tgacgcaaat | gggcggtagg | cgtgtacggt | gggaggtcta | tataagcaga | 180 |
| gctggtttag | tgaaccgtca | gatccgctag | cccaccatgt | ccatgttgtt | ctacactctg | 240 |
| atcactgcgt | ttttgatcgg | cgtacaggca | gaaccgtaca | cagatagcaa | tgtcccagaa | 300 |
| ggagactctg | tccctgaagc | ccactggact | aaacttcagc | attcccttga | cacagccctc | 360 |
| cgcagagccc | gcagtgcccc | tactgcacca | atagctgccc | gagtgacagg | gcagacccgc | 420 |
| aacatcactg | tagaccccag | actgtttaag | aaacggagac | tccactcacc | ccgtgtgctg | 480 |
| ttcagcaccc | agcctccacc | cacctcttca | gacactctgg | atctagactt | ccaggcccac | 540 |
| ggtacaatcc | ctttcaacag | gactcaccgg | agcaagcgct | ctgtgagtga | aatacagctt | 600 |
| atgcataacc | tgggaaaaca | tctgaactcg | atggagagag | tagaatggct | gcgtaagaag | 660 |

```
ctgcaggatg tgcacaattt tgttgccctt ggagctcctc tagctcccag agatgctggt    720
tcccagaggc ccgaaaaaa ggaagacaat gtcttggttg agagccatga aaaagtctt     780 ggagaggcag acaaagctga tgtgaatgta ttaactaaag ctaaatccca gtagctcgac    840
ctgcaggcat gcaagcttgg gatctttgtg aaggaacctt acttctgtgg tgtgacataa    900
ttggacaaac tacctacaga gatttaaagc tctaaggtaa atataaaatt tttaagtgta    960
taatgtgtta aactactgat tctaattgtt tgtgtatttt agattcacag tcccaaggct   1020
catttcagcc cctcagtcct cacagtctgt tcatgatcat atcagcatac acatttttgt   1080
agaggtttac tgctttaaaa acctcccaca cctcccctg aacctgaaac ataaaatgat    1140
gcattgttgt tgttacttgt ttatgcagct atatgtacaa taaagcatac attcaaatca   1200
caataagcat tttccggcat tcagtttggt tgttcaactc tatcaatggt atcctgtag    1259
```

<210> SEQ ID NO 4
<211> LENGTH: 736
<212> TYPE: PRT
<213> ORGANISM: Artificial Sequence
<220> FEATURE:
<223> OTHER INFORMATION: Synthetic

<400> SEQUENCE: 4

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Thr Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255
```

-continued

```
Tyr Lys Gln Ile Ser Asn Gly Thr Ser Gly Ser Thr Asn Asp Asn
                260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Gly Thr Lys Thr Ile Ala Asn
                325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
            405                 410                 415

Phe Glu Asp Val Pro Phe His Ser Ser Tyr Ala His Ser Gln Ser Leu
        420                 425                 430

Asp Arg Leu Met Asn Pro Leu Ile Asp Gln Tyr Leu Tyr Tyr Leu Val
            435                 440                 445

Arg Thr Gln Thr Thr Gly Thr Gly Thr Gln Thr Leu Ala Phe Ser
450                 455                 460

Gln Ala Gly Pro Ser Ser Met Ala Ser Gln Ala Arg Asn Trp Val Pro
465                 470                 475                 480

Gly Pro Ser Tyr Arg Gln Gln Arg Val Ser Thr Thr Asn Gln Asn
            485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
            515                 520                 525

Asp Asp Glu Asp Arg Phe Phe Pro Ser Ser Gly Val Leu Ile Phe Gly
530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
            565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
            595                 600                 605

Asn Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655

Asp Pro Pro Leu Thr Phe Asn Gln Ala Lys Leu Asn Ser Phe Ile Thr
            660                 665                 670
```

```
Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 5
<211> LENGTH: 3695
<212> TYPE: DNA
<213> ORGANISM: Artificial Sequence
<220> FEATURE:
<223> OTHER INFORMATION: Synthetic

<400> SEQUENCE: 5
```

| | | | | | |
|---|---|---|---|---|---|
| ctctttgcgc | ttgcgttttc | ccttgtccag | atagcccagt | agctgacatt | catccggggt | 60 |
| cagcaccgtt | tctgcggact | ggctttctac | gtgaaaagga | tctaggtgaa | gatccttttt | 120 |
| gataatctca | tgcctgacat | ttatattccc | cagaacatca | ggttaatggc | gttttttgatg | 180 |
| tcattttcgc | ggtggctgag | atcagccact | tcttccccga | taacggagac | cggcacactg | 240 |
| gccatatcgg | tggtcatcat | gcgccagctt | catccccga | tatgcaccac | cgggtaaagt | 300 |
| tcacgggaga | ctttatctga | cagcagacgt | gcactggcca | gggggatcac | catccgtcgc | 360 |
| cccggcgtgt | caataatatc | actctgtaca | tccacaaaca | gacgataacg | gctctctctt | 420 |
| ttataggtgt | aaaccttaaa | ctgccgtacg | tataggctgc | gcaactgttg | ggaagggcga | 480 |
| tcggtgcggg | cctcttcgct | attacgccag | ctggcgaaag | gggatgtgc | tgcaaggcga | 540 |
| ttaagttggg | taacgccagg | gttttcccag | tcacgacgtt | gtaaaacgac | ggccagtgaa | 600 |
| ttgtaatacg | actcactata | gggcgaattg | aatttagcgg | ccgcgaattc | gcccttatga | 660 |
| tatctggtgg | gaggagggca | agatgacggc | caaggtcgtg | gagtccgcca | aggccattct | 720 |
| cggcggcagc | aaagtgcgcg | tggaccaaaa | gtgcaagtcg | tccgcccaga | tcgatcccac | 780 |
| tcccgtcatt | gtcacctcca | acaccaacat | gtgcgccgtg | attgacggga | acagcaccac | 840 |
| cttcgagcac | cagcagccgt | tgcaggaccg | gatgttcaaa | tttgaactta | cccgccgtct | 900 |
| ggagcatgac | tttggcaagg | tgacaaagca | ggaagtcaaa | gagttcttcc | gctgggcgca | 960 |
| ggatcacgtg | accgaggtgg | cgcatgagtt | ccacgtcaga | agggtggag | ccaacaagag | 1020 |
| acccgccccc | gatgacgctg | ataaaagcga | gcccaagcgg | gcctgcccct | cagtcgcaga | 1080 |
| tccatcgacg | tcagacgcgg | aaggagctcc | ggtggacttt | gccgacaggt | accaaaacaa | 1140 |
| atgttctcgt | cacgcgggca | tgcttcagat | gctgtttccc | tgcaagacat | gcgagagaat | 1200 |
| gaatcagaat | ttcaacattt | gcttcacgca | cgggaccagg | gactgttcgg | agtgcttccc | 1260 |
| cggcgtgtca | gaatctcaac | cggtcgtcag | aaaaaggacg | tatcggaaac | tctgtgccat | 1320 |
| tcatcatctg | ctggggaggg | ctcccgagat | tgcttgctcg | gcctgcgatc | tggtcaacgt | 1380 |
| ggacctggat | gactgtgtct | ctgagcaata | aatgacttaa | accaggtatg | gctgccgatg | 1440 |
| gttatcttcc | agattggctc | gaggacaacc | tctctgaggg | cattcgcgag | tggtgggact | 1500 |
| tgaaacctgg | agccccgaaa | cccaaagcca | accagcaaaa | gcaggacgac | ggccggggtc | 1560 |
| tggtgcttcc | tggctacaag | tacctcgac | ccttcaacgg | actcgacaag | ggggagcccg | 1620 |
| tcaacgcggc | ggacgcagcg | gccctcgagc | acgacaaggc | ctacgaccag | cagctcaaag | 1680 |

| | |
|---|---|
| cgggtgacaa tccgtacctg cggtataacc acgccgacgc cgagtttcag gagcgtctgc | 1740 |
| aagaagatac gtcttttggg ggcaacctcg ggcgagcagt cttccaggcc aagaagcggg | 1800 |
| ttctcgaacc tctcggtctg gttgaggaag gcgctaagac ggctcctgga agaagagac | 1860 |
| cggtagagca gtcaccccaa gaaccagact cctcatcggg catcggcaag acaggccagc | 1920 |
| agcccgctaa aaagagactc aattttggtc agactggcga cacagagtca gtccccgacc | 1980 |
| cacaacctct cggagaacct ccagcagccc cctcaggtct gggacctaat acaatggctt | 2040 |
| caggcggtgg cgctccaatg cagacaata acgaaggcgc cgacggagtg ggtaattcct | 2100 |
| cgggaaattg gcattgcgat tccacatggc tgggggacag agtcatcacc accagcaccc | 2160 |
| gaacctgggc cctgcccacc tacaacaacc acctctacaa gcaaatctcc aacggcacct | 2220 |
| cgggaggaag caccaacgac aacacctact ttggctacag caccccctgg gggtattttg | 2280 |
| acttcaacag attccactgc cacttttcac cacgtgactg gcagcgactc atcaacaaca | 2340 |
| attggggatt ccggcccaag agactcaact tcaagctctt caacatccag gtcaaggaag | 2400 |
| tcacgacgaa cgaaggcacc aagaccatcg ccaataatct caccagcacc gtgcaggtct | 2460 |
| ttacggactc ggagtaccag ctaccgtacg tgctaggatc agctcaccag ggatgtctgc | 2520 |
| ctccgttccc ggcggacgtc ttcatggttc ctcagtacgg ttatctaact ctgaacaatg | 2580 |
| gcagccaggc cctgggacgt tcctccttct actgcctgga gtatttccca tcgcagatgc | 2640 |
| tgagaaccgg caacaacttt cagttcagct acaccttcga ggacgtgcct ttccacagca | 2700 |
| gctacgcgca cagccaaagc ctggacaggc tgatgaatcc cctcatcgac cagtacctgt | 2760 |
| attacctggt cagaacgcag acaaccggga ctggagggac gcagactctg gcattcagcc | 2820 |
| aagcaggccc tagctcaatg gccagccagg ctagaaactg ggtgcccgga ccgagctacc | 2880 |
| ggcagcagcg cgtctccacg acaaccaacc agaacaacaa cagcaacttt gcctggacgg | 2940 |
| gagctgccaa atttaaactg aacggccgag actctctaat gaaccccggc gtggccatgg | 3000 |
| cttcacacaa ggatgacgag gaccgcttct tcccttctag cggggtcctg attttcggca | 3060 |
| agcaaggagc cgggaatgat ggagtggatt acagccaagt gctgattaca gatgaggaag | 3120 |
| aaatcaaggc taccaacccc gtggcaacag aggaatatgg agcagtggcc atcaacaacc | 3180 |
| aggccgctaa tacgcaggcg cagaccggac tcgtgcacaa ccaggggtg attcccggca | 3240 |
| tggtgtggca gaacagagac gtgtacctgc agggtcccat ctgggccaaa attcctcaca | 3300 |
| cggacggcaa ctttcacccg tctcccctga tgggcggctt tggactgaag cacccgcctc | 3360 |
| ctcaaattct catcaagaac acaccggttc cagcggaccc gccgcttacc ttcaaccagg | 3420 |
| ccaagctgaa ctctttcatc acgcagtaca gcaccggaca ggtcagcgtg gaaatcgagt | 3480 |
| gggagctgca gaaagaaaac agcaaacgct ggaatccaga gattcagtac acttccaact | 3540 |
| actacaaatc tacaaatgtg gactttgctg tcaacacgga aggagtgtat agcgagcctc | 3600 |
| gccccattgg cacccgttac ctcacccgca acctgtaatt gcctgttaat caataaaccg | 3660 |
| gttaattcgt ttcagtaagg aagaattcgt ttaaa | 3695 |

<210> SEQ ID NO 6
<211> LENGTH: 736
<212> TYPE: PRT
<213> ORGANISM: Artificial Sequence
<220> FEATURE:
<223> OTHER INFORMATION: Synthetic

<400> SEQUENCE: 6

```
Met Ala Ala Asp Gly Tyr Leu Pro Asp Trp Leu Glu Asp Asn Leu Ser
1               5                  10                 15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Val Glu Gln Ser Pro Gln Glu Pro Asp Ser Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Ala Pro Ser Gly Leu Gly Pro Asn Thr Met Ala Ser Gly Gly Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Gly Thr Ser Gly Gly Ser Thr Asn Asp Asn
            260                 265                 270
Thr Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Thr Asn Glu Gly Thr Lys Thr Ile Ala Asn
                325                 330                 335
Asn Leu Thr Ser Thr Val Gln Val Phe Thr Asp Ser Glu Tyr Gln Leu
            340                 345                 350
Pro Tyr Val Leu Gly Ser Ala His Gln Gly Cys Leu Pro Pro Phe Pro
        355                 360                 365
Ala Asp Val Phe Met Val Pro Gln Tyr Gly Tyr Leu Thr Leu Asn Asn
    370                 375                 380
Gly Ser Gln Ala Leu Gly Arg Ser Ser Phe Tyr Cys Leu Glu Tyr Phe
385                 390                 395                 400
```

```
Pro Ser Gln Met Leu Arg Thr Gly Asn Asn Phe Gln Phe Ser Tyr Thr
            405                 410                 415

Phe Glu Asp Val Pro Phe His Ser Ser Tyr Ala His Ser Gln Ser Leu
        420                 425                 430

Asp Arg Leu Met Asn Pro Leu Ile Asp Gln Tyr Leu Tyr Tyr Leu Val
    435                 440                 445

Arg Thr Gln Thr Thr Gly Thr Gly Thr Gln Thr Leu Ala Phe Ser
450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Glu Asp Arg Phe Phe Pro Ser Ser Gly Val Leu Ile Phe Gly
    530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 7
<211> LENGTH: 365
<212> TYPE: DNA
<213> ORGANISM: Artificial Sequence
<220> FEATURE:
<223> OTHER INFORMATION: Synthetic

<400> SEQUENCE: 7
atgtccatgt tgttctacac tctgatcact gcgttttga tcggcgtaca ggcagaaccg      60
tacacagata gcaatgtccc agaaggagac tctgtccctg aagcccactg gactaaactt     120
cagcattccc ttgacacagc cctccgcaga gcccgcagtg cccctactgc accaatagct     180
```
gcccgagtga cagggcagac ccgcaacatc actgtagacc ccagactgtt taagaaacgg     240
agactccact caccccgtgt gctgttcagc acccagcctc cacccacctc ttcagacact     300
ctggatctag acttccaggc ccacggtaca atccctttca acaggactca ccggagcaag     360
cgctc                                                                 365

<210> SEQ ID NO 8
<211> LENGTH: 304
<212> TYPE: DNA
<213> ORGANISM: Artificial Sequence
<220> FEATURE:
<223> OTHER INFORMATION: Synthetic

<400> SEQUENCE: 8
tctgtgagtg aaatacagct tatgcataac ctgggaaaac atctgaactc gatggagaga      60
gtagaatggc tgcgtaagaa gctgcaggat gtgcacaatt tgttgccct tggagctcct     120 ctagctccca gagatgctgg ttcccagagg ccccgaaaaa aggaagacaa tgtcttggtt     180
gagagccatg aaaaaagtct tggagaggca gacaaagctg atgtgaatgt attaactaaa     240
gctaaatccc agtagctcga cctgcaggca tgcaagcttg ggatctttgt gaaggaacct     300
tact                                                                  304

<210> SEQ ID NO 9
<211> LENGTH: 736
<212> TYPE: PRT
<213> ORGANISM: Artificial Sequence
<220> FEATURE:
<223> OTHER INFORMATION: Synthetic

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Thr Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

-continued

```
Ala Pro Met Ala Asp Asn Asn Glu Gly Ala Asp Gly Val Gly Asn Ser
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Asn Gly Thr Ser Gly Ser Thr Asn Asp Asn
        260                 265                 270
Thr Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Thr Asn Gly Thr Lys Thr Ile Ala Asn
            325                 330                 335
Asn Leu Thr Ser Thr Val Gln Val Phe Thr Asp Ser Glu Tyr Gln Leu
            340                 345                 350
Pro Tyr Val Leu Gly Ser Ala His Gln Gly Cys Leu Pro Pro Phe Pro
        355                 360                 365
Ala Asp Val Phe Met Val Pro Gln Tyr Gly Tyr Leu Thr Leu Asn Asn
    370                 375                 380
Gly Ser Gln Ala Leu Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Thr
            405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Val
        435                 440                 445
Arg Thr Gln Thr Thr Gly Thr Gly Thr Gln Thr Leu Ala Phe Ser
    450                 455                 460
Gln Ala Gly Pro Ser Asn Met Ala Ser Gln Ala Arg Asn Trp Val Pro
465                 470                 475                 480
Gly Pro Ser Tyr Arg Gln Gln Arg Val Ser Thr Thr Thr Asn Gln Asn
            485                 490                 495
Asn Asn Ser Asn Phe Ala Trp Thr Gly Ala Ala Lys Phe Lys Leu Asn
            500                 505                 510
Gly Arg Asp Ser Leu Met Asn Pro Gly Val Ala Met Ala Ser His Lys
        515                 520                 525
Asp Asp Glu Asp Arg Phe Phe Pro Ser Ser Gly Val Leu Ile Phe Gly
    530                 535                 540
Lys Gln Gly Ala Gly Asn Asp Gly Val Asp Tyr Ser Gln Val Leu Ile
545                 550                 555                 560
Thr Asp Glu Glu Glu Ile Lys Ala Thr Asn Pro Val Ala Thr Glu Glu
            565                 570                 575
Tyr Gly Ala Val Ala Ile Asn Asn Gln Ala Ala Asn Thr Gln Ala Gln
        580                 585                 590
Thr Gly Leu Val His Asn Gln Gly Val Ile Pro Gly Met Val Trp Gln
        595                 600                 605
Asn Arg Asp Val Tyr Leu Gln Gly Pro Ile Trp Ala Lys Ile Pro His
610                 615                 620
```

Thr Asp Gly Asn Phe His Pro Ser Pro Leu Met Gly Gly Phe Gly Leu
625                 630                 635                 640

Lys His Pro Pro Gln Ile Leu Ile Lys Asn Thr Pro Val Pro Ala
            645                 650                 655

Asp Pro Pro Leu Thr Phe Asn Gln Ala Lys Leu Asn Ser Phe Ile Thr
                660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 10
<211> LENGTH: 27
<212> TYPE: DNA
<213> ORGANISM: Artificial Sequence
<220> FEATURE:
<223> OTHER INFORMATION: Synthetic

<400> SEQUENCE: 10
aagcaggccc tagcaacatg gccagcc                                    27

<210> SEQ ID NO 11
<211> LENGTH: 19
<212> TYPE: PRT
<213> ORGANISM: Artificial Sequence
<220> FEATURE:
<223> OTHER INFORMATION: Synthetic

<400> SEQUENCE: 11

Met Glu Phe Gly Leu Ser Trp Val Phe Leu Val Ala Leu Phe Arg Gly
1               5                   10                  15

Val Gln Cys

<210> SEQ ID NO 12
<211> LENGTH: 85
<212> TYPE: PRT
<213> ORGANISM: Artificial Sequence
<220> FEATURE:
<223> OTHER INFORMATION: Synthetic

<400> SEQUENCE: 12

Met Arg Phe Pro Ser Ile Phe Ala Val Val Phe Ala Ala Ser Ser Ala
1               5                   10                  15

Leu Ala Ala Pro Ala Asn Thr Thr Ala Glu Asp Glu Thr Ala Gln Ile
            20                  25                  30

Pro Ala Glu Ala Val Ile Gly Tyr Leu Gly Leu Glu Gly Asp Ser Asp
        35                  40                  45

Val Ala Ala Leu Pro Leu Ser Asp Ser Thr Asn Asn Gly Leu Ser Leu
    50                  55                  60

Ser Thr Asn Thr Thr Ile Ala Ser Ile Ala Ala Lys Glu Glu Gly Val
65                  70                  75                  80

Gln Leu Asp Lys Arg
            85